United States Patent [19]

Schmidt et al.

[11] 4,124,597
[45] Nov. 7, 1978

[54] PROCESS FOR MAKING (DL) PANTOLACTONE

[75] Inventors: Joachim Schmidt; Wolfgang Bamberg; Hartmut Grunert; Erhard Schorm; Christian Weigelt, all of Jena, German Democratic Rep.

[73] Assignee: VEB Jenapharm, Jena, German Democratic Rep.

[21] Appl. No.: 667,410

[22] Filed: Mar. 16, 1976

Related U.S. Application Data

[60] Continuation of Ser. No. 476,290, Jun. 4, 1974, abandoned, which is a division of Ser. No. 298,831, Oct. 19, 1972, abandoned.

[51] Int. Cl.² .......................................... C07D 307/32
[52] U.S. Cl. .............................................. 260/343.6
[58] Field of Search ................................... 260/343.6

[56] References Cited

U.S. PATENT DOCUMENTS

| | | | |
|---|---|---|---|
| 2,443,334 | 6/1948 | Van House | 260/343.6 |
| 2,702,816 | 2/1955 | Klein et al. | 260/343.6 |
| 2,863,878 | 12/1958 | Lynn | 260/343.6 |

Primary Examiner—Jane S. Myers
Attorney, Agent, or Firm—Michael J. Striker

[57] ABSTRACT

DL pantolactone is made by
(a) introducing isobutyraldehyde, formalin and sodium cyanide solution continuously at a predetermined rate into a circulation reactor, continuously circulating the said mixture in said reactor while cooling the circulating mass in a heat exchanger, thus continuously causing the heat generated in the reaction between the components of said mixture to be discharged in said heat exchanger and by continuously re-mixing the formed reaction product with the reaction components;
(b) continuously passing part of the reaction product into an after-treatment reactor where the said reaction is completed without re-mixing so as to form formisobutyraldolcyanohydrin;
(c) passing the latter product into a first reaction chamber, reacting therein the product with a continuously introduced non-oxidizing strong acid at an elevated temperature and pressure so as to hydrolyze the product, thus forming a solution of $\alpha,\gamma$-dihydroxy-$\beta,\beta$-dimethylbutyric acid;
(d) passing the said solution to a second reaction chamber and maintaining the solution therein at said elevated temperature and pressure until the $\alpha,\gamma$-dihydroxy-$\beta,\beta$-dimethylbutyric acid is lactonized to DL-$\alpha$-hydroxy-$\beta,\beta$-dimethyl-$\gamma$-butyrolactone and finally
(e) recovering the latter product from the acid solution.

The process permits obtaining DL-pantolactone in a continuous operation at a high yield.

14 Claims, 1 Drawing Figure

PROCESS FOR MAKING (DL) PANTOLACTONE

REFERENCES TO RELATED APPLICATIONS

This application is a continuation of application Ser. No. 476,290 filed June 4, 1974 which in turn was a division of application Ser. No. 298,831 filed Oct. 19, 1972. Both applications are now abandoned.

BACKGROUND OF THE INVENTION

The invention relates to a process and apparatus for the continuous making of DL-α-hydroxy-β,β-dimethyl-γ-butyrolactone (DL-pantolactone).

Pantolactone is of importance as one of the starting materials for the synthesis of DL-pantothenic acid, DL-Ca-pantothenate and pantothenylol (panthenol) as well as D(+)-pantothenic acid, D(+)-Ca-pantothenate and D(+)-pantothenylol. All these products have therapeutical value as vitamins.

Ordinarily DL-pantolactone is made in the following manner. Isobutyraldehyde is condensed with formaldehyde in the presence of an alkaline catalyst so as to form formisobutyraldol. The formisobutyraldol cyanohydrine which is obtained by the addition reaction between hydrocyanic acid and formisobutyraldol is then further hydrolyzed by heating with a mineral acid so as to form α, γ-dihydroxy-β,β-dimethylbutyric acid. The latter product can be converted by further heating with mineral acid without difficulty to the DL-pantolactone.

As a catalyst for making the formisobutyraldol potassium carbonate has been used. It has furthermore been found that the aldol condensation can also be catalyzed with alkali cyanides. This approach has been preferred because the next step thereafter is the addition reaction with hydrocyanic acid. The process is generally carried out at a temperature between 0° C. and 30° C. The reaction mass is usually left standing for a few hours.

Occasionally sodium bisulfite has been added in order to obtain the formisobutyraldol-bisulfite compound. Thus there were released only equivalent amounts of hydrocyanic acid from the added potassium cyanide. In another synthesis the formisobutyraldol and sodium cyanide containing reaction mass was neutralized with mineral acids and the required amount of hydrocyanic acid was thus released. The residence time in this case was between 5 and 15 hours.

In some processes the formed cyanohydrin was isolated by extraction with ether. However, normally the cyanohydrin was hydrolyzed without isolation by heating with concentrated or fuming hydrochloric acid to form α,γ-dihydroxy-β,β-dimethylbutyric acid which simultaneously was lactonized to the DL-pantolactone. In order to isolate the DL-pantolactone the reaction mass is then subjected to evaporation to dryness and the residue is extracted with acetone.

In another method the reaction mass was extracted directly with methylenechloride, ethylenechloride, ether or amylenehydrate. The crude DL-pantolactone thus obtained was recrystallized either from ether/petrol ether or was subjected to distillation in a vacuum.

In another prior art process the approach was this: A true solution made from isobutyraldehyde and formalin upon addition of methanol is added to an aqueous sodium cyanide solution and precautions are taken that the temperature in the reaction mixture does not exceed 20° C. The mixture is then permitted to stand for 2 hours. Subsequently it is neutralized with mineral acid and then further hydrolyzed to the α,γ-dihydroxy-β,β-dimethylbutyric acid and lactonized to DL-pantolactone by heating for 1 hr. at reflux temperature. The thus obtained DL-pantolactone is extracted by means of methylene chloride from the mixture and after evaporation of the solvent is converted with sodium hydroxide to sodium pantoate. The yield in this case is 62.3% of pure DL-pantolactone relative to the initial isobutyraldehyde.

Still another process proceeds by adding 37% formalin and methanol to an aqueous potassium carbonate solution and reacting the mixture dropwise at 25° C. with isobutyraldehyde and then stirring the mixture for 2 hr. at 25° C. and for 1 hr. at 35° C. The formisobutyraldol containing solution is then reacted during a period of 1 hr. at 5° to 10° C. in the presence of a $CaCl_2$ solution with a sodium cyanide solution and after stirring for 3 hrs. is neutralized with concentrated hydrochloric acid, hydrolyzed and lactonized to the DL-pantolactone. In this process a yield of 86% is obtained.

All these prior art processes have various shortcomings. The use of potassium carbonate for the separate condensation to formisobutyraldol increases the cost. Furthermore the isolation of formisobutyraldol and the making of the aldehyde-bisulfite compound do not result in any particular benefit. The long reaction time, and this includes the standing period on the shelf and the time for cooling the reaction mixture, which is necessary in the various stages of DL-pantolactone synthesis is the result of the discontinuous operation and is typical of all prior art processes. The practical performance of the synthesis thus becomes inconvenient and costly. The addition of $CaCl_2$ solution results in a higher yield of DL-pantolactone. However the shortcomings of the long reaction times apply also to this process. This process furthermore involves difficulties because of the formation of suspensions. Therefore, the present invention therefore has the object to provide for a continuous operation in order to obtain high yields of DL-pantolactone at a high performance rate per hour without having to cope with the above-listed difficulties.

SUMMARY OF THE INVENTION

The invention basically involves the introduction of the different components into a circulation reactor which is provided with a heat exchanger. The reaction mixture is thus continuously introduced into the reactor and the locally generated heat of reaction is immediately discharged by the intensive remixing of the reaction components with the reaction solution. The reaction is then completed in an aftertreatment reactor where no further remixing takes place. From there the reaction mixture is passed into a reaction chamber where a non-oxidizing strong acid is added to hydrolyze the formisobutyraldolcyanohydrin formed in the first stage to α,γ-dihydroxy-β,β-dimethylbutyric acid and this is followed by lactonizing the latter product to the DL-pantolactone at an elevated temperature and pressure. The desired DL-α-hydroxy-β,β-dimethyl-γ-butyrolactone is then recovered from the acid solution.

The invention also embraces an apparatus which basically includes the following parts: A circulation reactor, means for introducing the components into the reactor, a heat exchanger forming part of the circulation reactor, an aftertreatment reactor and a final reactor comprising dual reaction chambers with means for applying heat and pressure in the first chamber and maintaining the reaction product in the second chamber at such heat and pressure. The apparatus may also include a chamber for forming a premix of some of the components with a subsequent cooling device prior to the introduction into the circulation reactor. It may furthermore include a stripping column and pulsation column for recovering the final product from the solution.

BRIEF DESCRIPTION OF THE DRAWING

The drawing is a schematic flow-sheet illustrating the steps of the process of the invention.

DETAILS OF THE INVENTION AND PREFERRED EMBODIMENTS

Figure 1:
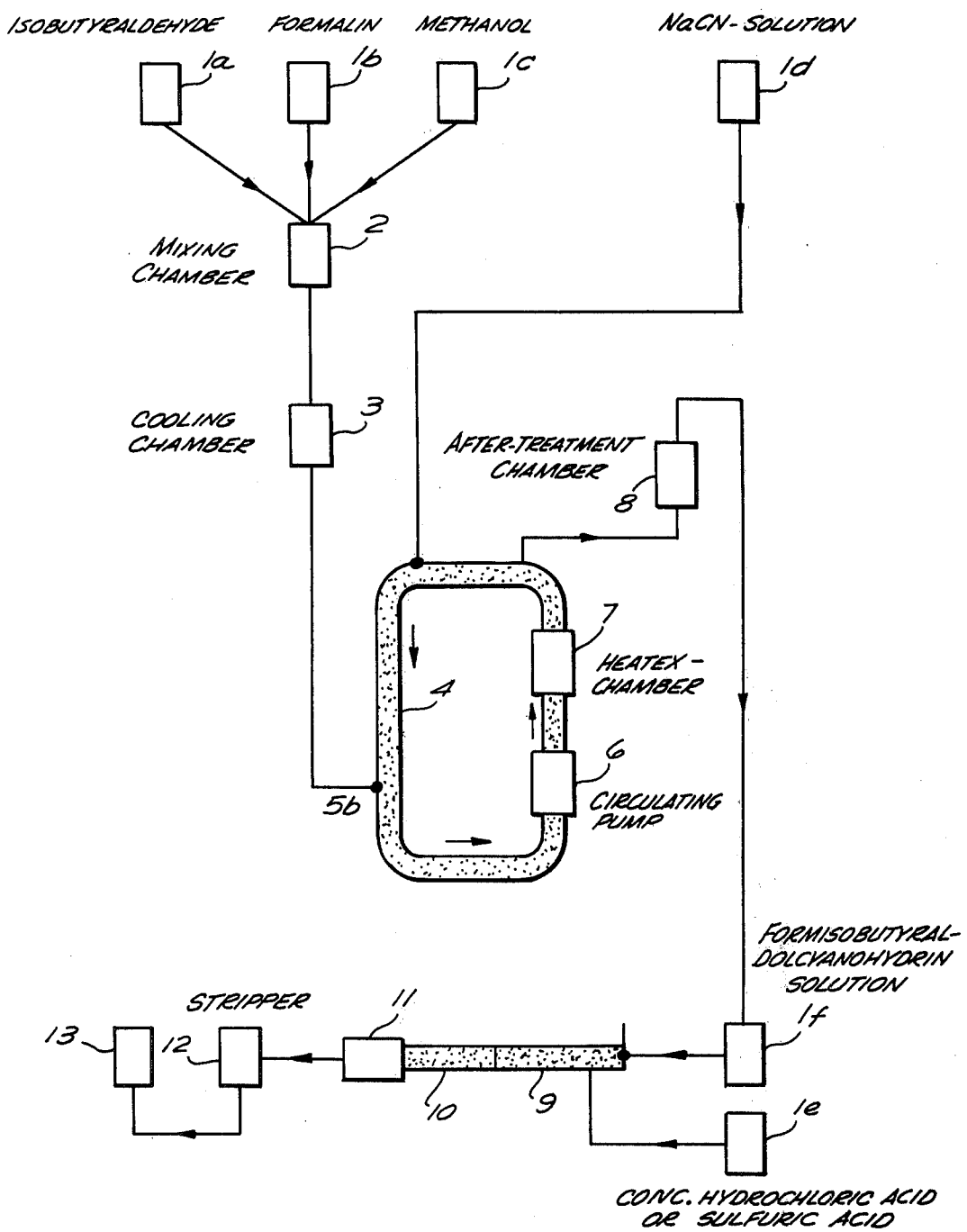

According to the process of the invention the formisobutyraldolcyanohydrin is made by introducing the components, that is a solution of sodium cyanide and a separate mixture of isobutyraldehyde, formalin and preferably a solution promoter by means of dosage pumps in a continuous manner into a circulation reactor. The circulation reactor is provided with suitable pump means for keeping the solution in continuous reaction. The mixture of isobutyraldehyde, formalin and, if such is used, the solution promoter, such as methanol, is cooled to room temperature before being introduced into the circulation reactor.

The reactor is provided with a heat exchanger which makes it possible to discharge the generated heat of about 30 Kcal/Mol by vigorous remixing of the components with the formed reaction solution. Thus excessive local heat development is avoided. This reduces the possibility of side reactions and the reverse reaction which occurs at equilibrium particularly at higher temperatures. Thus a substantially higher yield in formisobutyraldolcyanohydrin is obtained as against the discontinuous operation of prior art processes.

The reaction is preferably carried out at a temperature between 0° C. and 30° C. and most preferably at 20° C. The mean residence time in the circulation reactor is between 6 and 20 minutes and preferably is 10 minutes.

The reaction mixture is then passed into an aftertreatment vessel where it is slightly heated without any remixing. The residence time in this reactor is between 15 and 40 minutes preferably 25 minutes. Overall the process of the invention results in a shortening of the time necessary for formation of formisobutyraldolcyanohydrin by about 2.5 hrs., the reaction time being about 35 mins. at a substantially higher performance rate relative to the volume of the apparatus shown in the prior art.

The subsequent hydrolysis and lactonization of the formisobutyraldolcyanohydrin to the DL-$\alpha$-hydroxy-$\beta,\beta$-dimethyl-$\gamma$-butyrolactone (DL-pantolactone) according to the invention is effected in a tubular reactor of an acid resistant material. The hydrolyzing medium is a non-oxidizing strong acid, preferably, concentrated hydrochloric acid.

The solution of formisobutyraldolcyanohydrin is fed by means of pumps through a nozzle into the tubular reactor while at the same time mineral acid is added in measured amounts. The mixture of both components is effected in less than 0.1 min. The mass is then heated to 120°–150° C., preferably 130° C. The residence time at this temperature in the reactor is between 2 and 3 min. The pressure is between 15 and 20 atm. above atmospheric. The acid solution is discharged from the reactor by a pressure valve and in conventional manner is separated in a stripper column from the methanol, the methyl chloride which is formed as byproduct and final traces of hydrocyanic acid. It is then extracted in conventional form with an organic solvent.

The continuous operation of the invention is a tubular reactor under pressure as described permits operating with considerably higher temperatures than heretofore possible. The maximum may go up to the boiling temperature of the acidic mixture. Because of the high reaction temperature during the pantolactone formation the invention can proceed with the short residence time of a few minutes, thus resulting in a high performance rate per unit of time.

A further advantage of the process of the invention is the fact that the hydrocyanic acid which forms at the operating temperature and which in the prior art processes had to be subjected to separate destruction is simultaneously saponified. In the present process the use of closed system is considerably superior in regard to the health and safety of the personnel.

The yield of pantolactone relative to the initially employed isobutyraldehyde is between 75 and 80%.

The following Examples when read in conjunction with the accompanying drawings will further illustrate the invention:

EXAMPLE 1

5.45 l/hr. of formalin (30%), 5.35 l/hr. of isobutyraldehyde and 2.35 l/hr. of methanol were passed by dosage pumps 1a, 1b and 1c separately into a mixing chamber 2 in a continuous operation, were mixed therein and then cooled by means of the cooling device 3 to room temperature. The mixture was then introduced into a circulation reactor 4 of a capacity of 3.4 liters. Together with this mixture 9.25 l/hr. of a sodium cyanide solution were introduced from a dosage pump 1d. The solution had a concentration that was equivalent to 2.90 kg/hr. of NaCN. The injection into the circulation reactor was effected by means of nozzles 5a and 5b. The flow speed of the components in the nozzles was about 10 m/sec.

The circulation reactor was provided with a circulating pump 6 which generated a flow of 5,700 l/hr. The number of passes per hour of the components through the reactor was 260, the mean residence time of the components about 10 min. The heat exchanger 7 which formed part of the circulation reactor was provided with cooling liquid to an extent that the reaction temperature in the reactor did not exceed 20° C.

The reaction product discharged from the reactor was then passed into an aftertreatment vessel 8 after cooling it to 15° C. It passed through the aftertreatment vessel from the bottom up. The residence time in the vessel which had a capacity of 8.4 l was 25 min at a temperature of 15° to 20° C.

The completely reacted solution of formisobutyraldolcyanohydrin was then passed to a tubular reactor consisting of two sections, the first of which had an internal plated platinum lining. Simultaneously 12 l/hr. of concentrated hydrochloric acid ($d$ = 1.19) were passed into the reactor. The solution of formisobutyraldolcyanohydrin was injected by means of the dosage pump 1f through the nozzle 5c (diameter 0.6 mm, flow speed about 20 m/sec.). During that time the hydrochloric acid was injected by means of the dosage pump 1e. The pressure during the operation in the tubular reactor was between 15 and 20 atm. above atmospheric.

The first section 9 of the reactor which was provided with the internal platinum plating constituted a heat exchanger. The reaction mass was heated to 130° C. by external steam. In a second section 10 of the reactor which was provided at the inside only with a polytetrafluoroethylene coating served to maintain the reaction mixture at the previously reached temperature for between 2.1 and 2.5 min.

The diameter of the tubular reactor was 16 mm. The length of the heat exchanger portion was 3 m and the length of the final reaction chamber was 6 m. The hydrolyzed product after passing through the pressure valve 11 was then depressurized to atmospheric pressure and finally passed through a continuously operating column 12. The reaction product was separated in the column by steam stripping from the methanol and methyl chloride. The bottom product discharged from the column was cooled to room temperature and then passed to a continuously operating pulsation column 13 where it was extracted in countercurrent with chloroform by a liquid-liquid extraction.

6.9 to 7.3 kg of pantolactone was obtained hourly from the chloroform extract with a purity of 90%. This is equivalent to a yield of 75 to 80% of the theoretical yield relative to the initial isobutyraldehyde or NaCN.

EXAMPLE 2

The same process was used as in Example 1. However the starting product comprised 5.45 l/hr. of formalin (30%), 5.35 l/hr. of isobutyraldehyde, 9.25 l/hr. of NaCN solution and 12 l/hr. of concentrated hydrochloric acid. No solution promoter was used. There were obtained 7 kg pantolactone of a 90% purity. The yield was 76%.

EXAMPLE 3

The same process was used as in Example 1 except as follows: The starting product comprised 5.45 l/hr. of formalin (30%), 5.35 l/hr. of isobutyraldehyde, 2.35 l/hr. of methanol, 9.25 l/hr. of NaCN solution and 12 l/hr. of sulfuric acid (46%). The latter was used in the hydrolysis step. The residence time in the circulation reactor was 20 min. The temperature in the same reactor was 5° C. The time for the aftertreatment reaction was 40 min. The temperature in the tubular reactor was 150° C. and the residence time therein was 6 min. There were obtained 7 kg pantolactone of 90% purity. The yield was 76%.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. The process of making DL-α-hydroxy-β,β-dimethyl-γ-butyrolactone in a continuous operation comprising the steps, continuously performed, of
    (a) introducing isobutyraldehyde, formalin and a sodium cyanide solution continuously at predetermined rates into a circulation reactor constituting a closed system, circulating the said mixture in said reactor while cooling the circulating mass in a heat exchanger forming part of said circulation reactor, thus causing the heat generated in the reaction between the components of said mixture to be discharged through said heat exchanger during continuing circulation and causing continuous re-mixing of the formed reaction product with the said reaction components;
    (b) continuously passing reaction product formed in the circulation reactor into an after-treatment reactor where the reaction is completed without further mixing;
    (c) continuously passing reaction product in the form of formisobutyraldol-cyanohydrin from said aftertreatment reactor into a first reaction chamber, reacting therein the product with measured amounts of a continuously introduced non-oxidizing strong acid at an elevated temperature and pressure so as to hydrolyze the product, thus forming a solution of α-γ-dihydroxy-β,β-dimethylbutyric acid;
    (d) passing the latter solution into a second reaction chamber and maintaining the solution therein at said elevated temperature and pressure until the α-γ-dihydroxy-β,β-dimethylbutyric acid is lactonized to DL-α-hydroxy-β,β-dimethyl-γ-butyrolactone and finally
    (e) recovering the lactone from the acid solution.

2. The process of claim 1 wherein the strong acid introduced into the first reaction chamber is hydrochloric acid, and wherein the lactone formed in said second reaction chamber is separated from the methylchloride formed as byproduct and from residual hydrocyanic acid by steam stripping prior to extraction with an organic solvent.

3. The process of claim 1 wherein the temperature in the circulation reactor is between about 0° and 30° C. at a residence time between 6 and 20 minutes, wherein the residence time in the aftertreatment reactor is between about 15 and 40 minutes, and wherein the hydrolyzing and lactonizing reaction is effected at a pressure between about 15 and 20 atmospheres above atmospheric and during a residence time of about 2 to 6 minutes.

4. The process of claim 1 wherein the said first reaction chamber (at c of the claim) acts as heat exchanger between externally applied heat and the reaction mass in the chamber and wherein the second reaction chamber (at d of the claim) is provided with a heat insulation of the contents against the outside environment to substantially preserve the temperature generated in said first reaction chamber.

5. The process of claim 1 wherein methanol is added to the initial mixture as solution promoter.

6. The process of claim 1 wherein the reaction in the circulation reactor is carried out at a temperature between 0° and 30° C. and with a mean residence time of the components between 6 and 20 min.

7. The process of claim 6 wherein the temperature in the circulation reactor is 20° C. and the residence time is 10 min.

8. The process of claim 1 wherein the residence time in said aftertreatment vessel is 15 to 40 min.

9. The process of claim 8 wherein the residence time in said aftertreatment vessel is 25 min.

10. The process of claim 1 wherein the product is subjected, prior to introduction into said aftertreatment reactor, to cooling to a temperature lower than said temperature in the circulation reactor.

11. The process of claim 1 wherein the hydrolysis reaction and lactonizing reaction is effected at a pressure above the vapor pressure of the reaction mass at a temperature of 120° to 150° C. and a residence time of 2 to 6 min.

12. The process of claim 11 wherein the said pressure is between 15 and 20 atm. above atmospheric.

13. The process of claim 1 wherein said isobutyraldehyde and formalin are introduced into the circulation reactor as a premixture and said sodium cyanide solution is separately introduced into said circulation reactor.

14. The process of claim 13 wherein said premixture is cooled to room temperature prior to introduction into the circulation reactor.

* * * * *